United States Patent [19]

Mericle

[11] Patent Number: 4,478,218

[45] Date of Patent: Oct. 23, 1984

[54] LIGATING CLIP AND APPLIER INSTRUMENT THEREFOR WITH CLIP ENGAGING ESCAPEMENT

[75] Inventor: Robert W. Mericle, Lebanon, N.J.

[73] Assignee: Ethicon, Inc., Somerville, N.J.

[21] Appl. No.: 352,835

[22] Filed: Feb. 26, 1982

[51] Int. Cl.$^3$ ............................................. A61B 17/12
[52] U.S. Cl. ................................... 128/325; 128/346;
227/DIG. 1
[58] Field of Search .................. 128/325, 326, 334 R, 128/335, 335.5, 346; 227/DIG. 1, 19, DIG. 1 A, DIG. 1 B, DIG. 1 C, 117, 125; 29/243.56; 72/410

[56] References Cited

U.S. PATENT DOCUMENTS

| | | | |
|---|---|---|---|
| 3,006,344 | 10/1961 | Vogelfanger | 128/346 |
| 3,082,426 | 3/1963 | Miles | 227/DIG. 1 X |
| 3,780,416 | 12/1973 | Rider | 128/334 R X |
| 4,166,466 | 9/1979 | Jarvik | 227/19 X |
| 4,226,242 | 10/1980 | Jarvik | 128/325 |
| 4,294,355 | 10/1981 | Jewusiak et al. | 128/346 X |
| 4,316,468 | 2/1982 | Klieman et al. | 128/335 X |
| 4,325,376 | 3/1982 | Klieman et al. | 128/335 X |
| 4,372,316 | 2/1983 | Blake et al. | 128/325 |
| 4,380,238 | 3/1983 | Colucci et al. | 128/325 X |

FOREIGN PATENT DOCUMENTS 2069848 9/1981 United Kingdom ................ 128/326

*Primary Examiner*—C. Fred Rosenbaum
*Assistant Examiner*—Michelle Lester
*Attorney, Agent, or Firm*—Robert L. Minier

[57] ABSTRACT

A ligating clip is provided with first and second legs joined at their proximal ends by a hinge and terminating at their distal ends by a latch means for holding the clip latched closed when the legs are squeezed together. One of the legs is provided with a base defining guide means for engaging portions of an instrument that may be used to apply the clip. An instrument is provided to apply the clip and includes first and second handles mounted together for pivotal movement. Each handle extends beyond the pivot axis to form a clip closing jaw. The first handle includes a guideway for receiving a plurality of the open clips. A pusher member is provided within the first handle to push the clips to the jaw region. A spool is mounted for rotation in the first handle jaw and includes a forward flange and a rearward flange between which the front clip of the row of clips may be positioned. An L-shaped rod extends from the spool and is pivoted in one direction by one of the handles when the handles are closed to rotate the spool to permit passage of the closed clip from the jaws after the jaws are subsequently partially opened. The rod is also pivoted in a second, opposite direction after the handles are partially opened to orient the spool to block feeding of the next clip beyond the jaw region.

20 Claims, 22 Drawing Figures

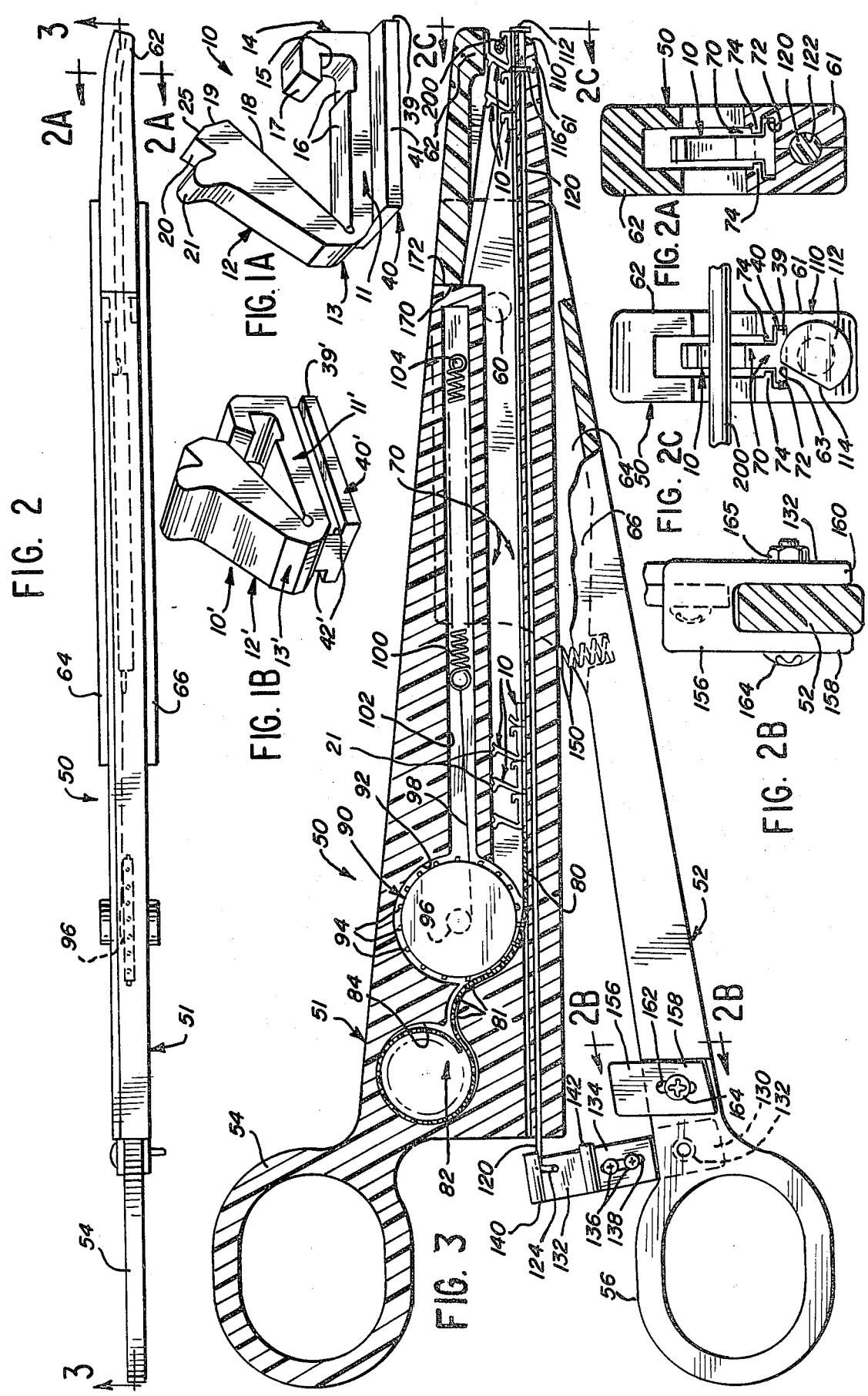

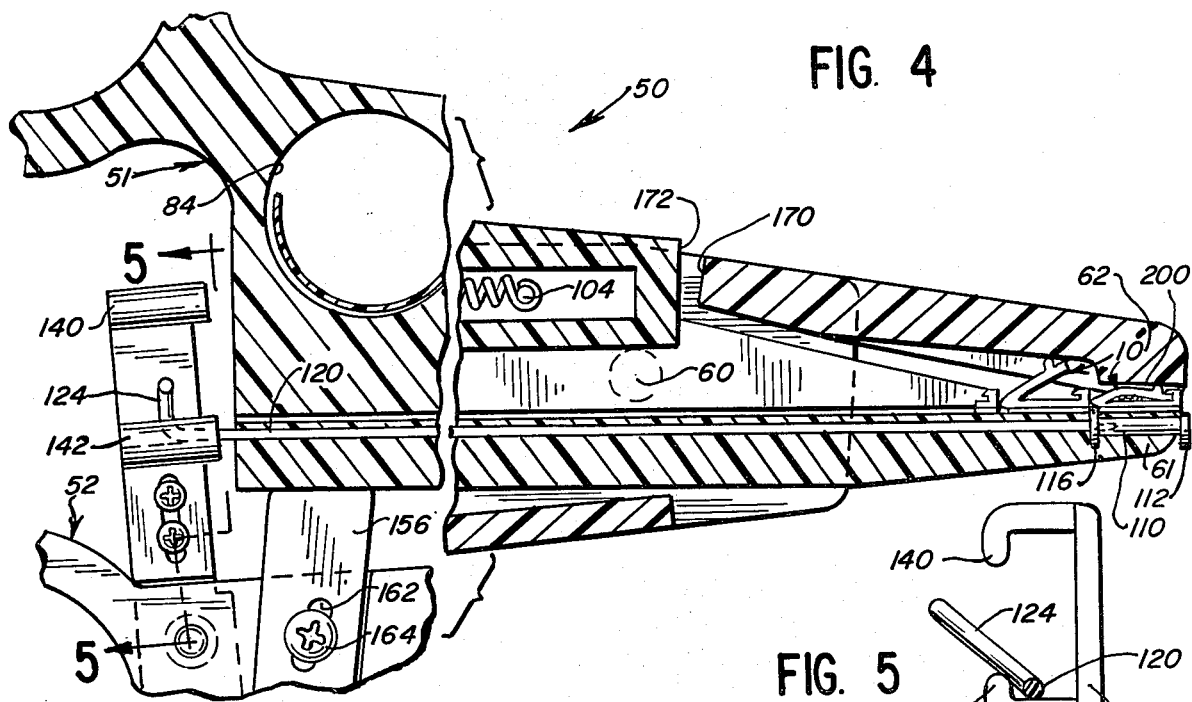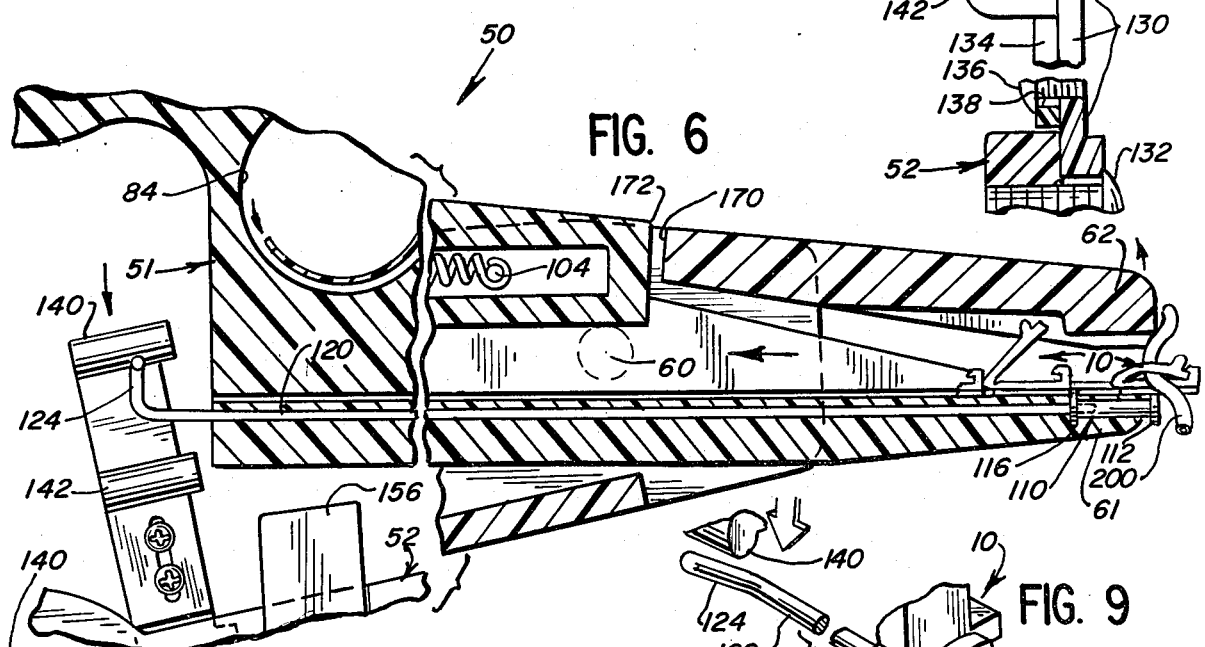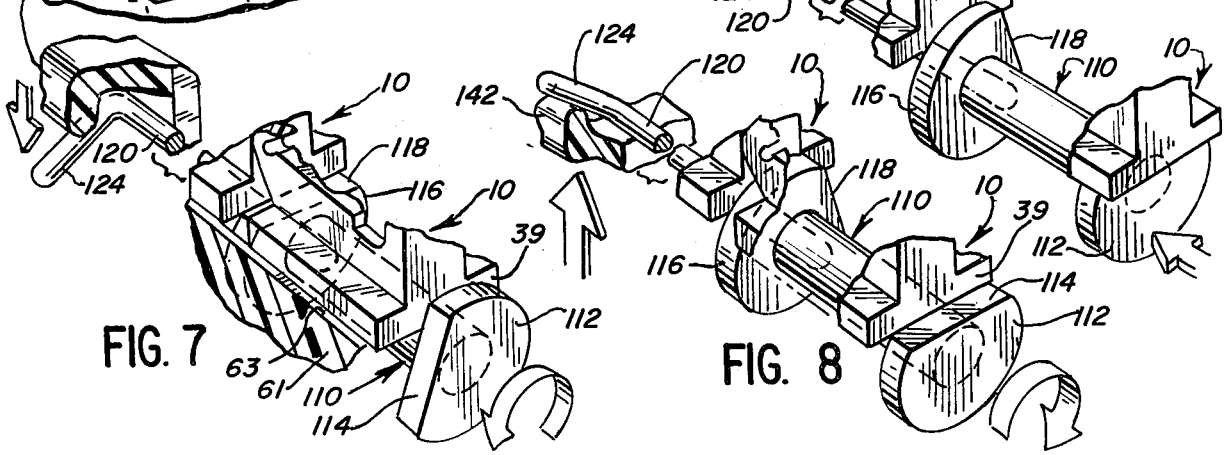

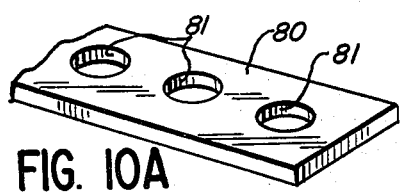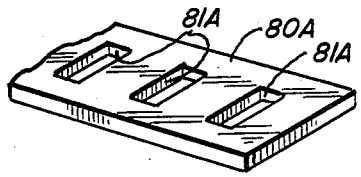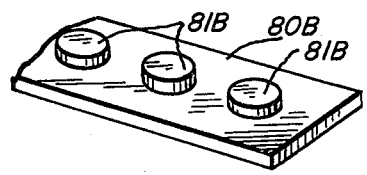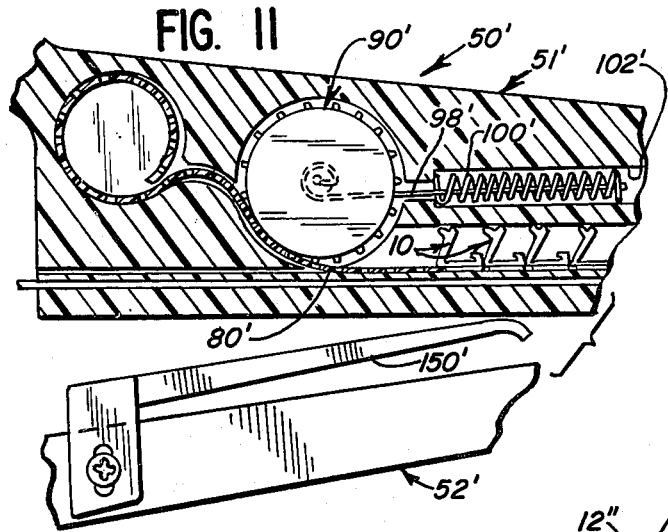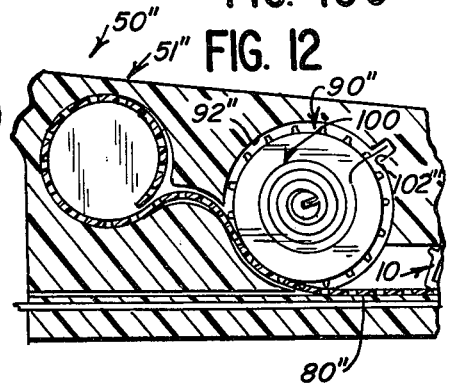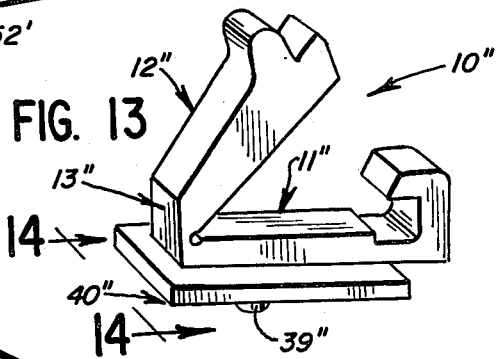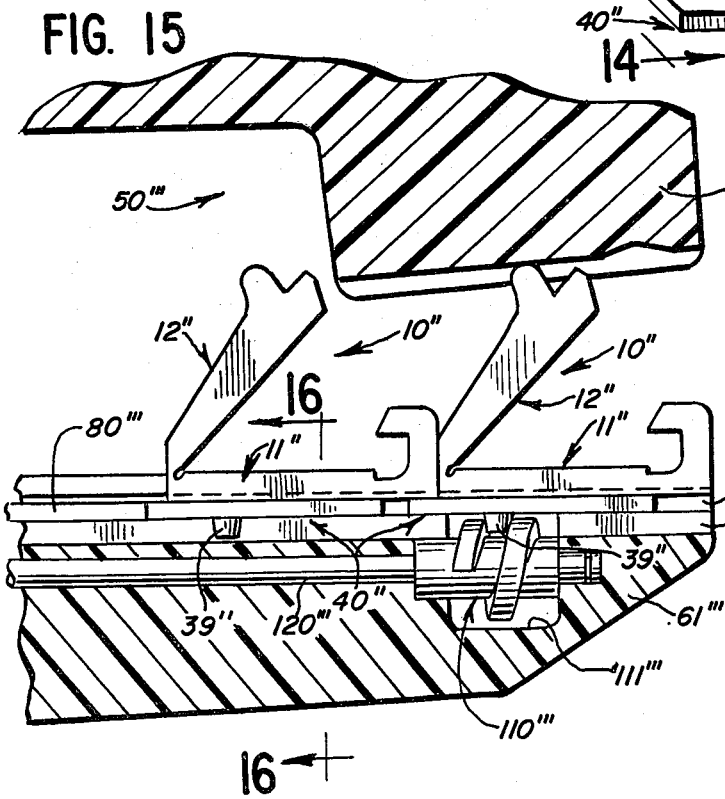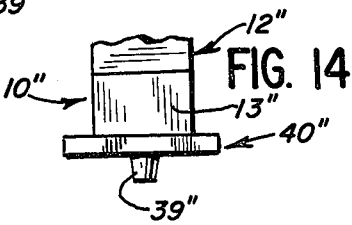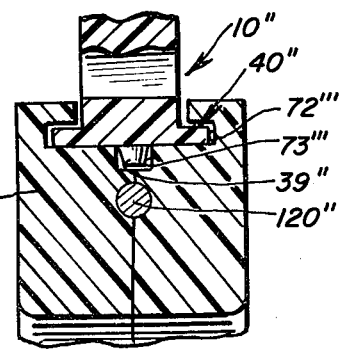

LIGATING CLIP AND APPLIER INSTRUMENT THEREFOR WITH CLIP ENGAGING ESCAPEMENT

DESCRIPTION

Technical Field

This invention relates to hemostatic or ligating clips and to surgical instruments for repeatedly applying such clips to tissue, blood vessels, and the like.

BACKGROUND OF THE INVENTION

Clips have been devised for clamping or strangulating various organs, vessels, and other tissue. Clips have been developed for use specifically in strangulating blood vessels in the human body. Such clips are known as hemostatic or ligating clips. The clips may be fabricated from absorbable or nonabsorbable polymeric materials as well as from metal.

A ligating clip is typically C-shaped, U-shaped, or V-shaped with two spaced-apart or diverging legs connected together at one end in a manner that permits the clip to be squeezed together so that the legs of the clip may be clamped around the tissue or blood vessel so as to tightly constrict the tissue or blood vessel. This prevents a substantial amount of fluid from passing through the tissue or blood vessel from one side of the closed clip to the other side of the closed clip.

Typically, the clip is made of a material and/or has a configuration that enables the clip, once it has been forced closed, to remain set or latched and maintain the closed orientation without outside intervention. For example, if the clip is made from a metal material, the clip can be deformed to the closed position. If the clip is made from a thermoplastic material, the legs may be connected by a resilient hinge portion and the distal ends of the legs may be provided with latch means for holding the legs together in a closed position when the legs of the clip are squeezed together around the tissue or blood vessel.

Various novel ligating clips are disclosed in copending U.S. patent applications assigned to the assignee of the present invention: Ser. No. 208,368, filed on Nov. 19, 1980; Ser. No. 276,131, filed on June 22, 1981; Ser. No. 277,582, filed on June 26, 1981; Ser. No. 277,454, filed on June 26, 1981; Ser. No. 282,461, filed July 13, 1981; and Ser. No. 296,672, filed on Aug. 27, 1981.

Some types of surgical clips have been proposed wherein one of the legs of the clip is especially adapted for being engaged by, and supporting the clip in, an applier instrument. See, for example, U.S. Pat. Nos. 3,780,416 and 3,882,854 which each disclose an asymmetric clip having two differently shaped legs with one of the legs being adapted to be received in a carrier or lower jaw of the applier instrument.

It would be desirable to provide a ligating clip which couldt be easily applied by an instrument to tissue, such as a blood vessel and the like. Further, it would be desirable to provide such a clip with a configuration that would permit a plurality of such clips to be loaded into, and contained within, the instrument for applying the clips. Further, it would be beneficial if the clip could be accommodated in the instrument and moved forward within the instrument to the clip applying jaws of the instrument by a relatively simple and trouble free mechanism. Also, it would be advantageous if such a clip had a configuration which would permit it to be restrained within the clip applying instrument and to be guided by the clip applying instrument to the jaws of the instrument.

A variety of instruments for applying such surgical clips have been developed or proposed in the past. A number of such instruments are discussed and disclosed in the copending patent application Ser. No. 208,368, filed on Nov. 19, 1980. Such instruments typically include a magazine or cartridge which may or may not be disposable and which holds a plurality of clips. The clips are supplied from the cartridge to jaws of the instrument one at a time for application to the tissue or blood vessel.

U.S. Pat. No. 3,006,344 discloses an instrument for applying a ligating clip to a blood vessel. The clip is formed of flat metal or like stock and has a pair of legs extending outwardly in a generally V-shape. The clips are arranged in two parallel grooves in a magazine. A slide is positioned in each groove and is urged by a suitable conventional spring to advance the clips along the magazine toward the jaws. The clips are arranged in each row with the distal end of one of the legs of one clip abutting the rear connecting hinge portion of the next adjacent clip.

U.S. Pat. No. 3,753,438 discloses an applicator for applying clips to suturing thread during the suturing of skin wounds. The clips are carried in a cartridge in the instrument. A clip is forced forwardly from the cartridge to a position between the instrument jaws by a slide which is operated by a handle. After the clip is positioned within the jaws, the handles of the instrument are squeezed together to squeeze the clip legs together.

It would be desirable to provide an improved instrument for accommodating a plurality of ligating clips and for automatically feeding the clips seriatim into jaws where a clip can be compressed about tissue, such as a blood vessel or the like. Further, it would be advantageous if the clips could be retained within the instrument and moved forward within the instrument toward the jaws of the instrument by an effective, yet relatively simple, mechanism. Additionally, it would be desirable to provide means in the instrument for ensuring that only one clip at a time is positioned in the jaws of the instrument for application to the tissue.

SUMMARY OF THE INVENTION

A preferred embodiment of the present invention is incorporated in a medical instrument for applying clips, including ligating clips made from a thermoplastic material. The clips each typically have two legs connected together at one end of the clip and are adapted to assume an initial open or spread apart configuration at the other end.

Each clip preferably includes first and second legs joined at their proximal ends by a resilient hinge and terminating at their distal ends in a latch means for holding the clip latched closed when the clip legs are squeezed together. Each leg has a vessel clamping inner face in opposition to a vessel clamping inner face of the other leg.

A base is provided on the clip first leg and extends along a length of the first leg from the distal end of the first leg for only a portion of the length of the leg. The base terminates short of the hinge so that the hinge extends rearwardly beyond the base to define an open recess adjacent the rearward end of the base below the hinge.

The base includes a guide means for engaging portions of an instrument that may be used to apply the clip. Such guide means can include a channel along each side of the clip base. Alternatively, such guide means can include portions of the base that extend laterally from the first leg on each side of the first leg. Another form of the clip may have a member projecting downwardly from the base to be engaged by an escapement mechanism in the clip applier instrument.

The preferred embodiment of the clip applying instrument includes first and second handles mounted together for pivotal movement about an axis. Each handle extends forwardly beyond the pivot axis to form a clip closing jaw. The jaws have opposing inner clip engaging faces.

The first handle includes a guideway for receiving a plurality of the opened clips in a single row with the clips arranged in end-to-end relationship with the distal end of the first leg of one clip abutting the leg connection end or hinge of the next forwardly adjacent clip. The first handle also includes a clip retaining means along the guideway for engaging the guide means of each clip.

In a preferred embodiment, the instrument is used with the type of clip in which the base has portions extending laterally outwardly from the first leg on each side of the first leg. The instrument guide means for retaining the clips in sliding engagement with the first handle includes opposed, spaced-apart, flanges or walls projecting inwardly from the guideway in the first handle. The flanges overlie the laterally outwardly projecting base portions of the clips and retain the clips within the guideway, permitting only forward or rearward movement of the clips within the guideway.

A means is provided for moving the clips forwardly along the guideway to the jaws. In the preferred embodiment, a flexible pusher member, such as a perforated tape, is provided within the first handle and extends into the guideway for pushing against the rear end of the base of the last clip in the row of clips within the clip guideway.

A means is provided for urging the flexible pusher member forwardly along the guideway to move the row of clips forwardly along the first handle to the jaws. In the preferred embodiment, wherein the pusher member is a perforated tape, the means for urging the pusher member forwardly includes a wheel mounted for rotation in the handle and having a plurality of circumferentially spaced and radially outwardly projecting pins. The pins are adapted to engage the apertures in the tape during rotation of the wheel. In order to advance the tape, the wheel is continuously urged to rotate by means of a cord that is wound around the hub of the wheel and that is pulled to unwind from the wheel hub by a tension spring secured at one end to the cord and at the other end to the instrument.

An escapement mechanism is provided in the first handle jaw to (1) properly position a clip in the jaws, (2) subsequently permit discharge of the clip after it has been latched closed while preventing discharge of the trailing, open clips, and (3) subsequently properly position the next clip in the jaws.

In a preferred embodiment of the instrument, the escapement includes a gate in the form of a spool is mounted for rotation about an axis in the first handle jaw below the clip engaging face of the first handle jaw. The spool is adapted to rotate between a first orientation and a second orientation. The spool includes a forward flange on a forward end adjacent the forward end of the first handle jaw. The forward flange projects in front of the guideway and defines a cut away segment to permit passage of a clip from the instrument when the spool is in the first orientation. The forward flange prevents passage of a clip therepast when the spool is in the second orientation.

The spool also has a rearward flange spaced from the forward flange by a distance equal to the length of the base of a ligating clip. The rearward flange projects into the guideway and defines a cut away segment that permits the passage of a clip therepast when the spool is in the second orientation and that prevents the passage of a clip therepast when the spool is in the first orientation.

A rod extends rearwardly from the spool along the first handle and is adapted to rotate about a longitudinal axis coincident with the longitudinal axis of the spool. The rod has a drive portion projecting laterally at an angle relative to the longitudinal axis of the rod.

An upper engaging member and a lower engaging member are carried by the second handle. The first and second engaging members are spaced apart and receive between them the drive portion of the rod. When the handles are moved apart, the upper engaging member engages the drive portion of the rod and rotates the rod to rotate the spool to the second orientation in which the forward flange blocks further forward feeding of the first clip in the row of clips to thereby maintain the first clip in the region of the jaws.

When the first and second handles are moved toward one another, the front clip in the row of clips within the region of the jaws is squeezed together and is latched closed. At the same time, the lower engaging member on the second handle engages the drive portion of the rod and rotates the rod to rotate the spool in a second, opposite direction to the first orientation in which the forward flange permits passage of the clip beyond the forward flange as the jaws are subsequently opened by moving the handles apart an amount sufficient to provide clearance around the closed clip but by an amount insufficient to again engage the drive portion of the rod with the upper engaging member.

Numerous other advantages and features of the present invention will become readily apparent from the following detailed description of the invention and embodiments thereof, from the claims and from the accompanying drawings.

BRIEF DESCRIPTION OF THE DRAWINGS

In the accompanying drawings forming part of the specification, and in which like numerals are employed to designate like parts throughout the same, FIG. 1A is a perspective view of a first embodiment of an open ligating clip of the present invention;

FIG. 1B is a perspective view of a second embodiment of an open ligating clip of the present invention;

FIG. 2 is a side view of a medical instrument for repeatedly applying a plurality of ligating clips of the type of the first embodiment illustrated in FIG. 1A;

FIG. 2A is a greatly enlarged, cross-sectional view taken generally along the plane 2A—2A in FIG. 2;

FIG. 2B is a greatly enlarged, fragmentary, cross-sectional view taken generally along the plane 2B—2B in FIG. 3;

FIG. 2C is a greatly enlarged end view taken generally along the plane 2C—2C in FIG. 3;

FIG. 3 is a top view of the instrument of FIG. 2 with a portion broken away and internal parts being illustrated in cross-section;

FIG. 4 is an enlarged, fragmentary view of the instrument illustrated in FIG. 3 but showing the instrument latching a clip closed about a blood vessel;

FIG. 5 is an enlarged, fragmentary, cross-sectional view taken generally along the planes 5—5 in FIG. 4;

FIG. 6 is a view similar to FIG. 4 but showing the instrument partially opened to permit the release of the latched closed clip;

FIGS. 7-9 are greatly enlarged, fragmentary, perspective views of the instrument with most of the jaw structure eliminated to better illustrate the escapement or gate mechanism, FIG. 7 showing the instrument in the fully opened position, FIG. 8 showing the instrument in the fully closed position, and FIG. 9 showing the instrument in the partially opened position;

FIGS. 10A, 10B, and 10C are enlarged, fragmentary, perspective views of first, second, and third embodiments, respectively, of a flexible pusher tape that may be used in various forms of the instrument of the present invention;

FIG. 11 is a fragmentary, reduced view similar to FIG. 3 but showing an alternate form of a means for driving the flexible pusher tape and an alternate form of a spring for biasing the instrument handles to an open position;

FIG. 12 is a fragmentary, reduced view similar to FIG. 3 but showing yet another alternate form of a means for driving the flexible pusher tape;

FIG. 13 is a perspective view of a third embodiment of an open clip of the present invention;

FIG. 14 is a fragmentary end view taken generally along the plane 14—14 in FIG. 13;

FIG. 15 is a fragmentary, cross-sectional view of the jaws of an instrument similar to the embodiment illustrated in FIG. 3 but showing an alternate form of the escapement mechanism; and FIG. 16 is a fragmentary, cross-sectional view taken generally along the plane 16—16 in FIG. 15.

DESCRIPTION OF THE PREFERRED EMBODIMENTS

While this invention is susceptible of embodiment in many different forms, there are shown in the drawings and will herein be described in detail preferred embodiments of the invention. It should be understood, however, that the present disclosure is to be considered as an exemplification of the principles of the invention and is not intended to limit the invention to the embodiments illustrated.

The precise shapes and sizes of the components herein described are not essential to the invention unless otherwise indicated. Unless otherwise indicated, the particular shapes and sizes are shown to best illustrate the principles of the invention.

A first preferred embodiment of the ligating clip 10 of the present invention is illustrated in FIG. 1A. The clip 10 has a first leg 11 and a second leg 12. The legs 11 and 12 of the open clip are joined at the leg connection end of the clips. Preferably, the legs 11 and 12 are joined at their proximal ends by a resilient hinge, hinge means, or hinge section 13 which permits the legs 11 and 12 to be pivoted toward each other to a closed position. Until the clip 10 is closed in a manner to be described in detail hereinafter, the hinge 13 has sufficient resiliency to maintain the legs 11 and 12 in the angled open position illustrated in FIG. 1A.

The first leg 11 terminates at the distal end thereof in a hook member 14 having a downwardly facing inner face 15 substantially parallel to an upwardly facing inner face 16 of the first leg 11 and forming an acute angle with an end face 17.

The second leg 12 terminates at the distal end in an end face 19 which forms an obtuse angle with an inner face 18 of the leg 12. The end face 19 of the second leg 12 is formed at an angle relative to a squared off face 25 which forms a substantially right angle with an upper surface 20.

The length and width of the face 16 of the first leg 11 and of the face 18 of the second leg 12 are substantially equal, and the face 15 of the hook member 14 is spaced from face 16 of the leg 11 by a distance corresponding to the thickness of the leg 12 between the plane of inner face 18 and upper surface 20.

The clip 10 can be closed or set by pivoting the legs 11 and 12 about hinge 13 to bring the faces 18 and 16 into opposition. The hook member 14 is deflected by the end face 19 of the second leg 12 until the distal end of the second leg 12 snaps under the hook member 14 and is thereby locked in place. Such a closure of the clip 10 is illustrated in FIG. 6 wherein the clip 10 is shown latched or locked closed about a blood vessel 200.

The end face 17 of the hook member 14 and the end face 19 of the second leg 12 are angled as illustrated to facilitate the passage of the second leg 12 past the hook member 14 during closure of the clip 10.

When the clip 10 is closed over a blood vessel 200 as illustrated in FIG. 6, the surfaces 16 and 18 engage and compress the vessel 200 to close the lumen thereof. The surfaces 16 and 18 may be smooth as illustrated in FIG. 1A, or may be provided with ridges or grooves to increase vessel holding power.

The first leg 11 may also be undercut at the juncture of the hook member 14 and the surface 16 as illustrated in FIG. 1A to increase deflectability of the hook member 14 and increase the space between the hook member 14 and the leg 11, thereby compensating for any inward deflection of the hook member 14 during closure of the clip which might reduce the clearance between the hook member surface 15 and the first leg surface 16 and otherwise interfere with the latching of the clip 10.

The clip 10 may also include an outside cylindrical boss 21 extending across the width of the second leg 12 near the distal end thereof. The boss 21 is spaced from surface 25 a distance sufficient to permit full engagement of the hook member 14 by the leg 12 when the clip 10 is in a closed and latched position.

The clip 10 is provided with a base 40 extending along the length of the first leg 11 from the distal end of the first leg 11 for only a portion of the length of the clip. The base 40 basically serves for being engaged by, and for supporting the clip 10 in, an instrument that may be used to apply the clip. One such instrument is discussed in detail hereinafter.

The base 40 terminates short of the leg connection end or resilient hinge 13 whereby the leg connection end or resilient hinge 13 extends rearwardly beyond the base 40 to define an open recess adjacent the rearward end of the base 40 below the hinge 13. At the front of the clip, the base 40 terminates in an engagement means or front face 39 (FIG. 7) that defines a plane generally normal to the length of the clip.

The base has a generally right rectangular prism or parallelpiped configuration with portions 41 of the base 40 extending laterally outwardly from the first leg 11 on each side of the first leg. The portions 41 of the base 40 extending laterally outwardly function as a guide means for engaging portions of the clip applier instrument as described in detail hereinafter.

FIG. 1B shows a second embodiment of a clip 10' that is similar to the clip 10 described above with reference to FIG. 1A. The clip 10' is illustrated as being a little shorter and a little wider than clip 10. The clip 10' includes a first leg 11' and a second leg 12' joined at their proximal ends by a resilient hinge 13' in the same manner as that discussed above for the legs 11 and 12 of the first embodiment of the clip 10 illustrated in FIG. 1A.

The basic structural features of the clip 10' in FIG. 1B are identical to that of the clip 10 illustrated in FIG. 1A except for the base 40' of the clip 10'. In the clip 10 illustrated in FIG. 1A, the base 40 extends laterally outwardly beyond the sides of the first leg 11. In contrast, the base 40' of the clip 10' illustrated in FIG. 1B does not extend beyond the sides of the first leg 11'. The width of the base 40' is the same as that of the first leg 11'.

Further, there is a channel 42' defined along the length of the base 40' on each side of the clip 10'. The channels 42' function as a guide means for engaging portions of an instrument that may be used to apply the clip 10'. Such an instrument, although not illustrated, is described hereinafter.

The clip 10' is illustrated as having slightly different proportions than clip 10. If desired, clip 10' may have the same proportions as clip 10 and may be the same size as, or a different size than, clip 10.

Each of the above-described novel clip structures, when fabricated from a suitable thermoplastic material, is biased to the open position by the resilient hinge portion. Thus, if force is applied to the distal ends of the legs of the open clip so as to move the legs toward one another (but not far enough to latch the clip), then upon removal of the force from the clip legs, the clip legs will return to the substantially fully open orientation.

It is believed that this phenomenon can be used to advantage in certain types of clip applier instruments for guiding and holding the clip in the instrument. Specifically, the legs of the clip may be deflected inwardly toward one another a small amount in a magazine, guide channel, or jaw structure of a clip applier instrument. Owing to the resilience of the hinge joining the two legs, the two legs will exert a force outwardly against the magazine, channel, or jaw structure to thereby provide a small friction holding force which may serve to help maintain the clip in the proper orientation or position within the instrument.

The above-described action of the resilient hinge plastic clip is in contrast with conventional ligating clips fabricated from relatively small diameter wire-like stock. Such metal clips can tolerate substantially no inward deflection of the legs without undergoing permanent deformation. Consequently, such metal clips exhibit no useful degree of resiliency and thus do not have the same inherent capability for providing the frictional holding force that is found in the above-described type of plastic clip.

A scissors-type medical instrument 50, generally illustrated in FIGS. 2 and 3, is adapted for holding a supply of ligating clips, each clip having the structure of the ligating clip 10 described above with reference to FIG. 1A, and for applying the clips seriatim to tissue.

The instrument has a first handle 51 and a second handle 52. The first handle 51 has a finger or thumb ring 54 and the second handle also has a finger or thumb ring 56. The first and second handles 51 and 52 are mounted together for pivotal movement about a pivot axis designated generally at reference numeral 60 in FIG. 3. Each handle 51 and 52 extends forwardly beyond the pivot axis 60 to form a clip closing jaw—a first handle lower jaw 61 and a second handle upper jaw 62 as illustrated best in FIG. 3. As can best be seen in FIG. 2, the jaws 61 and 62 are preferably curved toward one side.

The second handle 52 preferably has a pair of spaced-apart sidewalls 64 and 66 as best illustrated in FIGS. 2 and 3. The sidewalls 64 and 66 project upwardly and receive between them the first handle 51.

The first handle 51 defines a chamber, channel, or guideway 70 as best illustrated in FIG. 3 for receiving a plurality of the opened clips 10 in end-to-end relationship with the distal end of the first leg of one clip abutting the leg connection end or hinge of the next forwardly adjacent clip. As best illustrated in FIG. 2C, the clips 10 are received in the guideway 70 in a manner that permits forward movement of the clips 10 along the guideway 70.

Specifically, the guideway 70 includes a bottom channel 72 for receiving the base 40 of each clip 10. The instrument 50 includes inwardly projecting flanges 74 above the bottom channel 72. The flanges 74 of the guideway 70 function to engage the bases of the clips when the instrument 50 is tilted or turned to any position other than the horizontal position illustrated in FIG. 3. The flanges 74 can thus engage the bases of the clips and retain the clips within the instrument 50. The channel 72, in cooperation with the flanges 74, permits sliding movement of the clips 10 forwardly along the guideway 70.

As best illustrated in FIG. 3, when the clips 10 are disposed within the guideway 70 in the opened position, the boss 21 of each clip is in contact with the top of the guideway 70. Owing to the resilient nature of the clip hinge 13, the boss 21 of each clip is biased upwardly in the guideway 70. The clip bosses are thus forced against the top of the guideway 70 except in the region just forward of the pivot axis 60. At this point, the top of the guideway 70 terminates, since the first handle 51 extends forwardly of the pivot axis 60 only below the first handle 52.

The clips 10 are moved forwardly along the guideway 70 to the region of the jaws 61 and 62 by a novel flexible pusher member 80 as best illustrated in FIG. 3. The pusher member 80 is preferably a flexible, perforated tape defining a plurality of equally spaced apertures 81 extending along the length of the tape. As best illustrated in FIG. 10A, the flexible pusher member tape 80 preferably has a generally rectangular cross section and is adapted to be received within the channel 72. Preferably, a portion of the tape 80 is disposed in a spiral coil configuration 82 within a receiving chamber 84 in the first handle 51. A leading portion of the tape 80 is unwound from the spiral coil 82 and extends into the clip guideway 70 for abutting the rear end of the base 40 of the last clip in the row of clips within the guideway 70.

The instrument 50 further preferably includes a means for feeding the tape 80 forwardly along the guideway 70 to move the row of clips 10 forwardly along the first handle 51 to the jaws 61 and 62. Specifically, a sprocket wheel 90 is mounted for rotation relative to the first handle 51 within a cylindrical chamber 92. The sprocket wheel 90 has a plurality of circumferentially spaced and radially outwardly projecting pins 94 which are adapted to engage the perforations or apertures 81 in the tape 80.

As best illustrated in FIGS. 2 and 3, the sprocket wheel 90 includes a hub 96 for rotating with the wheel 90 relative to the first handle 51. A flexible cord 98 is wrapped or wound around the hub 96 and is secured to one end of a tension spring 100 disposed within a bore 102 in the first handle 51. The other end of the tension spring 100 is secured at post or pin 104 to the first handle 51. The spring 100 thus pulls the cord 98 from the hub 96 to thereby rotate the hub 96 and the wheel 90 to drive the tape 80 forwardly in the clip guideway 70.

A novel escapement mechanism is provided for preventing the clips 10 from being pushed out of the end of the jaws 61 and 62 until after the jaws are actuated and for ensuring that only one clip at a time is properly latched closed about a blood vessel 200 and discharged from the instrument 50. Specifically, with reference to FIGS. 2C, 3, and 7-9, a gate or spool 110 is mounted for rotation about a longitudinal axis in the first handle lower jaw 61 below the upwardly facing clip engaging face 63 (FIG. 2C) of the jaw 61. The spool 110 is adapted to rotate within the jaw 61 between a first orientation (FIGS. 4, 6, 8, and 9) and a second orientation (FIGS. 3 and 7).

The spool 110 has a forward flange 112 on the forward end adjacent the forward end of the first handle jaw 61. The forward flange 112 projects in front of the guideway 70 and defines a segment cut away at face 114 (FIG. 8) to permit passage of a clip 10 when the spool 110 is in the first orientation.

The spool 110 has a rearward flange 116 which is spaced from the forward flange 112 by a distance equal to the length of the base 40 of clip 10. The rearward flange 116 projects into the guideway 70 and defines a segment cut away at face 118 (FIG. 7) to permit passage of a clip 10 therepast when the spool 110 is in the second orientation.

As best illustrated in FIG. 8, when the spool 110 is in the first orientation to permit passage of a clip 10 past the first flange 112, the second flange 116 is oriented to block passage of the next rearward clip into the jaw region. Similarly, when the spool 110 is in the second orientation illustrated in FIG. 7 wherein the forward flange 112 blocks the guideway, the rearward flange 116 is oriented to permit passage therepast of a clip into the jaw region behind the forward flange 112.

As best illustrated in FIG. 3, a rod 120 extends rearwardly from the spool 110 within a cylindrical bore 122 (FIG. 2A) in the first handle 51 and is adapted to rotate about a longitudinal axis coincident with the longitudinal axis of the spool 110. As best illustrated in FIGS. 3 and 5, the rod 120 extends beyond the rear end of the first handle 51 and has a laterally projecting drive portion 124. The laterally projecting drive portion 124 is disposed at a 90 degree angle relative to the longitudinal axis of the rod 120.

A novel actuating structure is provided for engaging the drive portion 124 of the rod 120 and for rotating the drive portion 124, the rod 120, and the spool 110 so as to orient the spool 110 in either the first orientation (FIGS. 4, 6, 8, and 9) or the second orientation (FIGS. 3 and 7). Specifically, as best illustrated in FIGS. 3 and 5, a plate structure 130 is mounted to the second handle 52 by means of a screw 132. Another plate 134 is secured to the plate 130 by means of two screws 136 (FIG. 3). The screws 136 extend through an elongate slot 138 in the plate 134 and are threadingly engaged in the plate 130. The heads of the screws 136 engage the surface of the plate 134 around the slot 138. The slot 138 permits the plate 134 to be adjusted vertically relative to the plate 130.

The plate 130 has at its top end an upper engaging member 140 and the plate 134 has at its top end a lower engaging member 142. The upper engaging member 140, the lower engaging member 142, and the plate 130 together define a generally C-shaped configuration.

The upper engaging member 140 is adapted to engage and pivot the drive portion 124 of the drive member 120 from the upwardly inclined orientation illustrated in FIG. 5 to the downwardly inclined orientation illustrated in FIG. 3. Conversely, the lower engaging member 142 is adapted to engage and pivot the drive portion 124 of the rod 120 from the downwardly inclined orientation illustrated in FIG. 3 to the upwardly inclined orientation illustrated in FIG. 5. As the drive portion 124 of the rod 120 is pivoted between these two orientations, the rod 120 the spool 110, necessarily rotate about the longitudinal axis.

As best illustrated in FIGS. 7 and 8, there is a particular relationship between the laterally angled drive portion 124, the spool rearward flange 116, and the spool forward flange 112. This can be seen with reference to FIGS. 3 and 7 which illustrate the instrument when the handles 51 and 52, and hence the jaws 61 and 62, are in a fully opened position. In this position, the upper engaging member 140 has engaged the drive portion 124 and pivoted the drive portion 124 to the downwardly inclined orientation. This rotates the spool 110 to the second orientation wherein the forward flange 112 prevents forward movement of a clip out of the region of the jaws. Specifically, the clip engagement means or front face 39 of the base is engaged by, or abuts, the flange 112.

In FIGS. 4 and 8, the handles 51 and 52 are closed and the lower engaging member 142 has engaged and pivoted the drive portion 124 of the rod 120 to the upwardly inclined orientation. This rotates the spool 110 to the first orientation in which the forward flange 112 permits passage of a clip out of the jaw region.

When the handles 51 and 52 are not being held closed, they are normally urged to the outwardly open position illustrated in FIG. 3 by a helical compression spring 150 disposed between the first and second handles 51 and 52 rearwardly of the pivot axis 60. When the handles 51 and 52 are squeezed together, overcoming the biasing effect of the spring 150, the closure movement is limited by an abutment member 156 as best illustrated in FIG. 2B and FIG. 4. Specifically, the abutment member 156 is mounted to the second handle 52. To this end, the abutment member 156 has a saddle-shaped configuration with a first leg 158 on one side of the second handle 52 and with a second leg 160 on the other side of the second handle 52. Each leg 158 and 160 of the abutment member 156 defines an elongate slot, such as the slot 162 visible in FIGS. 3 and 4 in the leg 158. The slots are in registry and permit the passage therethrough of a screw 164. The screw 164 is secured with a nut 165 which is against the leg 160 of the abutment member 156. The slots, such as slot 162, permit adjustment of the abutment member 156 on the second handle 52.

When the handles 51 and 52 are squeezed together as illustrated in FIG. 4, the abutment member 156 abuts the bottom surface of the first handle 51 and prevents further closure movement. This limits the closure of the jaws 61 and 62 and also prevents the lower engaging member 142 from pivoting the drive portion 124 of the rod 120 beyond the angle illustrated in FIGS. 4 and 5.

The handles 51 and 52 cannot be opened any further than shown in FIG. 3. This is because an abutment face 170 (FIGS. 3 and 4) behind the upper jaw 62 of the second handle 52 engages an abutment 172 on the first handle 51 above, and slightly forward of, the pivot axis 60. This prevents the upper engaging member 140 from pivoting the drive portion 124 of the rod 120 beyond the angled position illustrated in FIG. 3.

The sequence of operation of the instrument 50 will next be described in detail. When the instrument 50 is in the fully opened position illustrated in FIG. 3, the spool 110 is in the second orientation wherein the forward flange 112 blocks the further forward feeding of the clips 10. In this position, the drive portion 124 of the rod 120 is in its most downwardly inclined orientation. Further, in this position, the flexible tape 80 urges the row of clips 10 forwardly so that the distal end of the first leg of each clip abuts the hinge of the next forwardly adjacent clip.

As illustrated in FIGS. 3 and 7, the front clip 10 in the row of clips is positioned between the open jaws 61 and 62 but is prevented from moving further forwardly by the flange 112 on the spool 110. The distal end of the first leg of the next rearwardly adjacent clip abuts the hinge of the front clip. Owing to the fact that the base 40 of the front clip terminates short of the hinge 13 of the front clip, there is an open recess beneath the hinge of the front clip between the rear end of the base 40 of the front clip and the front end of the base of the next rearwardly adjacent clip. This open recess can accommodate the subsequent rotation of the spool rearward flange 116 between the two clips.

With the front clip 10 positioned in the open jaws 61 and 62 as illustrated in FIGS. 3 and 7, the instrument 50 may be carried by the surgeon to the region of the blood vessel 200. The instrument 50 is positioned so that the jaws 61 and 62 locate the first, open clip 10 about the blood vessel 200. Next, the surgeon closes the handles 51 and 52 together to squeeze the clip closed as illustrated in FIG. 4. As this occurs, the lower engaging member 142 engages and pivots the drive portion 124 of the drive rod 120 into the upwardly inclined orientation illustrated in FIGS. 4 and 8. The maximum closure is determined by the abutment of the member 156 with the bottom of the first handle 51 as illustrated in FIG. 4.

When the instrument 50 has been fully closed as illustrated in FIG. 4, the spool 110 has necessarily been rotated from the second orientation to the first orientation wherein the forward flange 112 of the spool 110 will now permit passage of the front, closed clip beyond the forward flange 112. The rearward flange 116 has been simultaneously rotated into position to block the forward movement of the next rearwardly adjacent clip. However, at this point, the jaws 61 and 62 are still closed and thus the instrument 50 cannot yet be disengaged from the closed clip 10.

The instrument 50 is removed from the closed clip 10 and ligated blood vessel 200 by subsequently partially opening the handles 51 and 52 to thereby partially open the jaws 61 and 62. This is illustrated in FIGS. 6 and 9 where the handles 51 and 52 have been partially opened so that the jaws 61 and 62 are spaced apart an amount sufficient to provide clearance around the latched closed clip 10. However, the handles 52 and 52 have been opened an amount insufficient to engage the drive portion 124 of the rod 120 with the upper engaging member 140. So long as the drive portion 124 is not engaged and pivoted by the upper engaging member 140, the spool 110 remains in the first orientation to (1) permit passage of the closed clip beyond the forward flange 112 and (2) block movement of the next rearwardly adjacent clip into the jaw region.

With the instrument 50 partially open as illustrated in FIGS. 6 and 9, the instrument 50 is withdrawn by the surgeon from the region of the ligated blood vessel 200. As the instrument 50 is being withdrawn, or after the instrument 50 has been completely withdrawn, from the latched closed clip about the vessel 200, the handles 51 and 52 may be further opened to the fully opened position illustrated in FIGS. 3 and 7. In this fully open position, the upper engaging member 140 has engaged and pivoted the drive portion 124 of the rod 120 to rotate the spool 110 to the second orientation wherein the rearward flange 116 permits passage of the next clip 10 into the jaw region but prevents passage of that clip out of the jaw region beyond the blocking forward flange 112. The clips 10 in the row in the guideway 70 are urged forwardly by the tape 80 so that the new first or front clip becomes properly positioned within the jaw region in abutting relationship with the blocking forward flange 112. The instrument 50 is now ready for applying this clip.

Although the preferred embodiment of the pusher member 80 has been illustrated as a perforated tape having apertures 81 to receive the wheel drive pins 94, it is to be realized that the tape may instead be slotted, embossed, or otherwise provided with suitable means for being engaged by a rotating wheel structure similar to the wheel 90.

One such alternate embodiment of the pusher member 80 is illustrated in FIG. 10B and is designated generally therein by reference numeral 80A. The pusher member 80A is a flexible tape having a generally rectangular cross section and defining therein a plurality of spaced-apart rectangular apertures 81A. The instrument 50 illustrated in FIGS. 2 and 3 could be modified for use with such a tape 80A by providing the wheel 90 with rectangular prism projections instead of the cylindrical pins 94.

Another alternate form of the pusher member 80 is shown in FIG. 10C and is designated generally therein by the reference numeral 80B. The pusher member 80B is a flexible tape having a generally rectangular cross section. The tape 80B does not have apertures. Rather, the tape 80B is provided with spaced-apart, upwardly projecting cylindrical bosses 81B. The tape 80B could be used with the instrument 50 illustrated in FIGS. 2 and 3 if the wheel 90 were modified to replace the pins 94 with cylindrical recesses for receiving the bosses 81B.

Although the preferred embodiment has been illustrated with the drive wheel 90 being rotated by the cord 98 which is connected to the helical tension spring 100, it is to be realized that other suitable mechanisms for rotating the wheel 90 may be employed.

Specifically, FIG. 11 illustrates an alternate form of a means for driving the flexible pusher tape within an alternate embodiment of the instrument designated generally by reference numeral 50'. The instrument 50' is generally similar to the first embodiment of the instrument 50 described above with reference to FIGS. 2 and 3. The instrument 50' includes a first handle 51' and a second handle 52'. A cavity 102' is provided within the first handle 51' for receiving a compression spring 100'. The compression spring 100' bears at its rearward end against the first handle 51' and is secured at its forward end to a cord 98'. The cord 98' is secured to the hub of a wheel 90' that is identical to the wheel 90 described above with reference to the first embodiment of the instrument 50 illustrated in FIGS. 2 and 3.

Since the compression spring 100' is biased forwardly along the first handle 51', the cord 98' is continuously urged to unwind from the wheel 90', thus advancing a perforated flexible tape 80' that pushes against the last clip 10.

The embodiment of the instrument 50' illustrated in FIG. 11 may also have a metal or plastic leaf spring 150', as illustrated, in place of the helical compression spring 150 used in the first embodiment of the instrument 50 illustrated in FIGS. 2 and 3. The leaf spring 150' may be fabricated from a thermoplastic material, and if desired, may be integrally molded from the thermoplastic material with either of the handles 51' and 52'.

FIG. 12 illustrates another embodiment 50" of an instrument for applying clips 10. The instrument 50" in FIG. 12 is substantially similar to the first embodiment of the instrument 50 illustrated in FIGS. 2 and 3, except that the mechanism for advancing the pusher tape is different. Specifically, the instrument 50" in FIG. 12 has a first handle 51" with a chamber 92" for receiving a wheel 90" that is substantially identical to the wheel 90 in the first embodiment of the instrument 50 illustrated in FIGS. 2 and 3. As in the first embodiment, the wheel 90" of this alternate embodiment is engaged with a flexible pusher tape 80" for advancing the flexible pusher tape 80" along the first handle 51" and against the last clip 10 in the row of clips. The chamber 92" also receives a clock spring 100" which is secured at its inner end to the hub of the wheel 90" and which is restrained at its outer end in a small cavity 102". Thus, the clock spring 100" continuously urges the wheel 90" to rotate and advance the flexible pusher tape 80" against the last clip 10 in the row of clips.

Although the pusher member embodiments have been described above as being formed from a *flexible* tape, it is to be realized that the pusher member 80 may be a *rigid* member and that the means for advancing the pusher member along the guideway 70 may include a suitable spring mechanism in place of the wheel 90 and cord 98.

In the illustrated preferred embodiment of the instrument 50, the spool 110 is shown with a forward flange 112 and a rearward flange 116. It is to be realized that other gate-type configurations may also be used.

The instrument 50 can be modified to accommodate the second embodiment of the clip 10' discussed above with reference to FIG. 1B. Specifically, the cross section of the guideway 70 (illustrated in FIG. 2A) in the lower jaw 61 can be modified to accept the clip 10' (FIG. 1B) instead of the clip 10 (FIG. 1A). Specifically, with the clip 10', there is no need to provide the wider, lower channel 72 in the guideway 70. Instead, the guideway 70 can have a constant width from top to bottom except where the flanges 74 project inwardly. The flanges 74 can be positioned slightly lower in the guideway 70 so as to enter into the channels 42' of the clip 10'. Of course, the width of the guideway 70 would be such as to accommodate the actual width clip 10' (which may be narrower or wider than clip 10). Also, the distance between the spool flanges 112 and 116 would be such as to properly accommodate the length of the clip 10'.

A third embodiment of a clip, similar to clip 10 illustrated in FIG. 1A is illustrated in FIGS. 13 and 14 and is designated generally therein by reference numeral 10". The clip 10" includes a first leg 11" and a second leg 12" joined at their proximal ends by a resilient hinge 13" and functions in the same manner as discussed above for the first embodiment of the clip 10 illustrated in FIG. 1A.

The basic structural features of the clip 10" in FIG. 13 are identical to that of clip 10 illustrated in FIG. 1A except for the base 40" of the clip 10". In the clip 10 illustrated in FIG. 1A, the base 40 extends to the distal end of the first leg 11 but terminates short of the resilient hinge 13. In contrast, the base 40" of the clip 10" illustrated in FIG. 13 does not extend all the way to the front or distal end of the first leg 11". Further, the base 40" extends rearwardly *beyond* the first leg 11" and hinge 13".

The base 40" can be regarded as having an upper portion with a generally right rectangular prism configuration and an associated engagement means 39" that comprises a lower portion of the base projecting from the upper portion and having a length less than the length of the upper portion. Preferably, the engagement means 39" is a frustoconical projection below the upper portion of the base 40".

A novel instrument 50''' is illustrated in FIGS. 15 and 16 for applying the clip 10". The instrument includes an upper jaw 62''' and a lower jaw 61'''. The lower jaw 61''' extends from a first handle (not visible in FIG. 15) that is similar to the first handle 51 of the embodiment of the instrument 50 illustrated in FIG. 3. Similarly, the upper jaw 62''' extends from a second handle (not visible in FIG. 15) that is similar to the second handle 52 of the first embodiment of the instrument 50 illustrated in FIG. 3. The basic construction of the instrument 50''' is similar to the first embodiment of the instrument 50 described above with reference to FIG. 3 except that the escapement means and the escapement actuator of the instrument 50''' are different than the escapement means or spool 110 and the escapement actuator of the first embodiment of the instrument 50.

Specifically, the instrument 50''' is provided with an escapement means in the form of a worm gear 110''' disposed in the recess 111''' in the lower jaw 61'''. A rod 120''' extends rearwardly from the worm gear 110''' in the same manner as the rod 120 of the first embodiment of the instrument 50 described above with reference to FIG. 3. However, the rearward end of the rod 120''' is connected with a suitable conventional mechanism (not illustrated in FIGS. 15 and 16) which 1) effects a rotation of the worm gear in only one direction and only when the jaws are being moved open and 2) causes no rotation of the worm gear 110''' when the jaws are being moved closed. Portions of such a conventional actuating mechanism may be mounted on the handles associated with the jaws 61''' and 62''' so as to convert the opening motion of the handles to a one-way rotation of the rod 120'''. The mechanism would be inoperative as the handles are being closed.

As in the case of the first embodiment of the instrument 50 described above with reference to FIG. 3, the embodiment of the instrument 50′′′ includes a flexible pusher tape 80′′′ to push the clips 10″ forwardly into the region of the jaws 61′′′ and 62′′′. As best illustrated in FIG. 16, the base 40″ of each clip is received within a channel 72′′′ of the lower jaw 61′′′. The lower jaw 61′′′ also defines a second channel 73′′′ opening upwardly to the first channel 72′′′. The frustoconical engagement means 39″ of each clip 10″ is received within the channel 73′′′.

As best illustrated in FIG. 15, the clips are aligned in end-to-end relationship and the hinge portion of each clip is abutted by the forward distal end portion of the first leg 11″ of the next rearwardly adjacent clip. In operation, the flexible pusher tape 80′′′ pushes the row of clips along the instrument 50′′′ to maintain the engagement means 39″ of the front clip in the row in engagement with the thread on the worm gear 110′′′. In FIG. 15, the jaws 61′′′ and 62′′′ are shown partially closed with the front clip 10″ positioned between the jaws and ready to be squeezed closed about a blood vessel (not shown). At this point, the jaws have been moved together a small amount sufficient to just bring the upper jaw 62′′′ into contact with the top of the clip second leg 12″.

With the instrument oriented as illustrated in FIG. 15, the clip 10″ may be located about a blood vessel and then the instrument 50′′′ may be actuated to fully close the jaws and latch the clip 10″ about the vessel. As the jaws are closed, the rod 120′′′ and the worm gear 110′′′ are not rotated, since the above-described actuating mechanism (not illustrated) does not operate to effect rotation of the rod 120′′′ during the closing movement of the jaws.

After the clip 10″ has been latched closed about the blood vessel, the jaws are opened and the actuating mechanism then operates the rod means 120′′′ to rotate the worm gear 110′′′ in a direction to advance the front clip 10″ out of the jaw 61′′′. As the jaws 61′′′ and 62′′′ are continued to be moved to the fully opened position, the next rearwardly adjacent clip 10″ is urged into engagement with the still rotating worm gear 110′′′ for direct advancement by the worm gear. When the jaws 61′′′ and 62′′′ have been moved to the full open position (further apart than shown in FIG. 15), the new front clip has been moved into the middle of the worm gear thread (the fully advanced position illustrated for the front clip 10″ in FIG. 15) and the rotation of the worm gear 110′′′ terminates.

Subsequent partial closure of the jaws may be effected (without rotating the worm gear 110′′′) to bring the upper jaw 62′′′ into contact with the new front clip second leg 12″ as illustrated in FIG. 15. The new front clip is then ready to be applied to a blood vessel.

With the novel escapement mechanism of the instrument 50′′′, it is seen that as the latched closed front clip is positively ejected from the instrument 50′′′ (first by the worm gear 110′′′ and finally by the tape-driven advancement of the entire row of clips). However, the next rearwardly adjacent (open) clip in the instrument cannot also be inadvertently ejected from the instrument since the next clip is necessarily first engaged by the worm gear 110′′′ within the jaws.

The embodiments of the instrument of the present invention may be used to apply other types of clips having an appropriate base structure, including metal clips. For example, such clips, while not having a resilient hinges, may be formed of tantalum or stainless steel. These clips could be deformed into the closed position and would possess sufficient strength to retain the deformation when clamped about a duct, such as a blood vessel.

From the foregoing, it will be observed that numerous variations and modifications may be effected without departing from the true spirit and scope of the novel concept of the invention. It is to be understood that no limitation with respect to the specific apparatus illustrated herein is intended or should be inferred. It is, of course, intended to cover by the appended claims all such modifications as fall within the scope of the claims.

What is claimed is:

1. A scissors-type medical instrument for repeatedly applying a plurality of ligating clips seriatim about tissue wherein each said clip is initially provided in an open state and wherein each said clip comprises first and second legs joined at their proximal ends by a resilient hinge and spaced apart at their distal ends with said legs having latch means at said distal ends for holding said clip closed in clamping engagement about said tissue when said legs are squeezed together, each said clip having a base extending along said first leg from the distal end of said leg and terminating short of said clip hinge whereby said hinge projects rearwardly of said base to define an open recess adjacent the rearward end of said base below said hinge, said clip base including guide means for slidably engaging a portion of said instrument, said instrument comprising:

first and second handles mounted together for pivotal movement about a pivot axis, each said handle extending forwardly beyond the pivot axis to form a clip closing jaw, said jaws having opposing clip engaging faces;

said first handle including a guideway for receiving a plurality of said open clips in a single row with the clips arranged in end-to-end relationship with the distal end of said first leg of one clip abutting the hinge of the next forwardly adjacent clip, said first handle including clip retaining means along said guideway for engaging said clip base guide means to retain said clip in sliding engagement within said first handle in said guideway;

means for moving said row of clips forwardly along said guideway to said jaws;

a gate at said first handle jaw mounted for rotation about a longitudinal axis between a first orientation and a second orientation, said gate including a forward flange adjacent the forward end of said first handle jaw, said forward flange projecting in front of said guideway and defining a segment cut away to permit passage of a clip therepast when the gate is in said first orientation but preventing the passage of a clip therepast when said gate is in said second orientation, said gate having a rearward flange spaced rearwardly from said forward flange by a distance substantially equal to the length of the base of a clip, said rearward flange projecting into said guideway and defining a segment cut away to permit the passage of a clip therepast when said gate is in said second orientation but preventing the passage of a clip therepast when said gate is in said first orientation;

a rod extending rearwardly from said gate along said first handle and adapted to rotate about a longitudinal axis coincident with the rotational axis of said gate, said rod having a drive portion projecting laterally at an angle relative to the longitudinal axis of said rod; and an upper engaging member carried by said second handle and a lower engaging member carried by said second handle, said first and second engaging members being spaced apart and receiving between them said drive portion of said rod whereby, (1) when said first and second handles are moved apart, said upper engaging member engages said drive portion of said rod and rotates said rod in a first direction to rotate said gate to said second orientation in which said forward flange blocks further forward feeding of the first clip in the row of clips and thereby maintains said first clip in the region of said jaws and, (2) when said first and second handles are moved toward one another, the front clip in the row of clips within the region of the jaws is squeezed together and latched closed and said lower engaging member engages said drive portion of said rod and rotates said rod to rotate said gate in a second, opposite direction to said first orientation in which said forward flange permits passage of said closed clip beyond said forward flange as said jaws are subsequently opened by moving said handles apart an amount sufficient to provide clearance around the closed clip but by an amount insufficient to again engage said drive portion of said rod with said upper engaging member.

2. The instrument in accordance with claim 1 in which said means for moving said row of clips includes:
a pusher member carried by said instrument and extending into said clip guideway for pushing against the rear end of the base of the last clip in the row of clips within said clip guideway; and
means for urging said pusher member forward along said guideway.

3. The instrument in accordance with claim 2 in which said pusher member is a flexible tape having a generally rectangular cross section and defining a plurality of equally spaced apertures extending along the length of the tape, a portion of the length of said tape being disposed in a spiral coil configuration within said first handle and a leading portion of said tape being unwound from said spiral coil and extending into said clip guideway for abutting the rear end of the base of the last clip in the row of clips within said clip guideway; and
in which said pusher member urging means comprises:
(a) a wheel mounted for rotation in said first handle, said wheel having a plurality of circumferentially spaced and radially outwardly projecting pins, each said pin being adapted to engage an aperture in said tape, said wheel including a hub for rotating with said wheel relative to said first handle;
(b) a tension spring having first and second ends, said tension spring being mounted at a first end to said first handle member; and
(c) a cord wrapped around said wheel hub at one end of the cord and secured at the other end to said second end of said tension spring whereby said cord is pulled to unwind from said hub to thereby rotate said wheel to urge said tape forward in said clip guideway.

4. The instrument in accordance with claim 1 in which said second handle further includes an abutment member for engaging said first handle member and limiting the closure movement of said first and second handle members.

5. The instrument in accordance with claim 1 further including means for biasing said handles apart a distance sufficient to open said jaws for releasing a closed clip.

6. The instrument in accordance with claim 5 in which said handle biasing means includes a helical compression spring disposed between said first and second handles rearwardly of said pivot axis.

7. The instrument in accordance with claim 1 in which said instrument is adapted to apply clips in which the base of each said clip extends laterally outwardly from said first leg and in which clip guideway includes a channel with inwardly projecting flanges adapted to extend over said laterally extending portions the clip bases to aid in retaining the clips in the instrument.

8. The instrument in accordance with claim 1 further including a support structure projecting upwardly from said second handle for supporting said upper and lower engaging members and which together with said engaging members define a generally C-shaped configuration.

9. The instrument in accordance with claim 1 in which said gate is a generally cylindral spool with said rearward flange at one end and with said forward flange at the other end.

10. A scissors-type medical instrument for holding a plurality of ligating clips and for applying the clips seriatim about tissue wherein each said clip is initially provided in an open state and wherein each said clip comprises first and second legs joined at their proximal ends by a resilient hinge and spaced apart at their distal ends with said legs having latch means at said distal ends for holding said clip closed in clamping engagement about said tissue when said legs are squeezed together, each said clip having a base extending along said first leg from the distal end of said leg and terminating short of said clip hinge whereby said hinge projects rearwardly of said base to define an open recess adjacent the rearward end of said base below said hinge, said clip base including guide means for slidably engaging a portion of said instrument, said instrument comprising:
first and second handles mounted together for pivotal movement about a pivot axis, each said handle extending forwardly beyond the pivot axis to form a clip closing jaw, said jaws having opposing clip engaging faces;
said first handle including a guideway for receiving and holding a plurality of said open clips in a single row with the clips arranged in end-to-end relationship with the distal end of said first leg of one clip abutting the hinge of the next forwardly adjacent clip, said first handle having inwardly projecting flanges along said guideway for engaging said clip base guide means to retain each said clip in sliding engagement within said first handle in said guideway;
a flexible, perforated tape carried by said instrument and extending into said clip guideway for pushing against the rear end of the base of the last clip in the row of clips within said clip guideway;
a wheel mounted for rotation in said first handle, said wheel having a plurality of circumferentially spaced and radially outwardly projecting pins, each said pin being adapted to engage a perforation in said tape, said wheel including a hub for rotating with said wheel relative to said first handle;

a tension spring having first and second ends, said tension spring being mounted at a first end to said first handle member;

a cord wrapped around said wheel hub at one end of the cord and secured at the other end to said second end of said tension spring whereby said cord is pulled to unwind from said hub to thereby rotate said wheel to urge said tape forward in said clip guideway to move said row of clips forwardly along said guideway to said jaws;

a cylindrical spool in said first handle jaw mounted for rotation about a longitudinal axis between a first orientation and a second orientation, said spool including a forward flange adjacent the forward end of said first handle jaw, said forward flange projecting in front of said guideway and defining a segment cut away to permit passage of a clip therepast when the spool is in said first orientation but preventing the passage of a clip therepast when said spool is in said second orientation, said spool having a rearward flange spaced rearwardly from said forward flange by a distance substantially equal to the length of the base of a clip, said rearward flange projecting into said guideway and defining a segment cut away to permit the passage of a clip therepast when said spool is in said second orientation but preventing the passage of a clip therepast when said spool is in said first orientation;

a rod extending rearwardly from said spool along said first handle and adapted to rotate about a longitudinal axis coincident with the rotational axis of said spool, said rod having a drive portion projecting laterally at an angle relative to the longitudinal axis of said rod; and an upper engaging member carried by said second handle and a lower engaging member carried by said second handle, said first and second engaging members being spaced apart and receiving between them said drive portion of said rod, whereby 1) when said first and second handles are moved apart, said upper engaging member engages said drive portion of said rod and rotates said rod in a first direction to rotate said spool to said second orientation in which said forward flange blocks further forward feeding of the first clip in the row of clips and thereby maintains said first clip in the region of said jaws and (2) when said first and second handles are moved toward one another, the front clip in the row of clips within the region of the jaws is squeezed together and latched closed and said lower engaging member engages said drive portion of said rod and rotates said rod to rotate said spool in a second, opposite direction to said first orientation in which said forward flange permits passage of said closed clip beyond said forward flange as said jaws are subsequently opened by moving said handles apart an amount sufficient to provide clearance around the closed clip but by an amount insufficient to again engage said drive portion of said rod with said upper engaging member.

11. In a ligating clip comprising first and second legs joined at their proximal ends by a resilient hinge and terminating at their distal ends in latch means for holding the clip latch closed when the clip legs are squeezed together, each leg having a vessel clamping inner face in opposition to a vessel clamping inner face of the other leg, the improvement characterized in that:

said clip includes a base extending along the length of said first leg from the distal end of said first leg for only a portion of the length of the clip, said base terminating short of the resilient hinge whereby said resilient hinge extends rearwardly beyond said base to define an open recess adjacent the rearward end of said base below said hinge, said base further including (1) a front engaging face and (2) guide means for each being engaged by portions of an instrument that may be used to apply said clip, said guide means including a channel on each side of said clip that is defined along the length of the base.

12. The clip in accordance with claim 11 in which said base has a generally right rectangular parallelpiped configuration and in which said guide means includes a portion of said base extending laterally outwardly from said first leg on each side of said first leg.

13. The clip in accordance with claim 12 in which said first leg terminates at the distal end thereof in a deflectable hook member extending from the inner face of said first leg, said hook member having an inner face spaced from and substantially parallel to the inner face of said first leg; and in which said second leg terminates at the distal end thereof in a surface adapted to deflect said hook member and enter the space between the inner face of said hook member and the inner face of said first leg whereby, when said first and second legs are pivoted closed about said hinge, the distal end of said second leg deflects and engages the hook member of said first leg to latch the clip closed.

14. A scissors-type medical instrument for repeatedly applying a plurality of ligating clips seriatim about tissue wherein each said clip is initially provided in an open state and wherein each said clip comprises first and second legs joined at their proximal ends by a resilient hinge and spaced apart at their distal ends with said legs having latch means at said distal ends for holding said clip closed in clamping engagement about said tissue when said legs are squeezed together; each said clip including a base extending along a portion of said first leg and including means for being guided and retained by, and for supporting said clip in, said instrument; each said clip also including engagement means associated with said base for being engaged by said instrument, said instrument comprising:

first and second handles mounted together for pivotal movement about a pivot axis, each said handle extending forwardly beyond the pivot axis to form a clip closing jaw, said jaws having opposing clip engaging faces;

said first handle including a guideway for receiving a plurality of said open clips in a single row with the clips arranged in end-to-end relationship with the distal end of said first leg of one clip abutting the hinge of the next forwardly adjacent clip, said first handle including clip retaining means along said guideway for engaging said clip base to retain said clip in sliding engagement within said first handle in said guideway;

means for moving said row of clips forwardly along said guideway to said jaws;

an escapement means at said first handle jaw for engaging said clip engagement means to prevent the passage of the front clip therepast until the jaws have latched the front clip closed and for accommodating movement of the front clip therepast after the jaws have latched the front clip closed;

rod means extending rearwardly from said escapement means along said first handle for being operated to move said escapement; and operating means carried by said second handle for operating said rod means whereby, (1) when said first and second handles are moved apart a sufficient amount, said escapement positions said front clip in the region of said jaws and prevents discharge of the front clip from the jaws and, (2) after said first and second handles are moved toward one another to latch the front clip closed and before said handles are again moved apart said sufficient amount, said escapement means permits discharge of said closed front clip from said jaws while preventing positioning in said jaws of the next rearwardly adjacent clip.

15. The instrument in accordance with claim 14 in which said escapement means includes a worm gear mounted for rotation in said first handle jaw for engaging said engagement means of said clip with the worm gear thread.

16. The instrument in accordance with claim 14 in which said means for moving said row of clips forwardly includes a pusher member in said first handle for pushing against the last clip in the guideway, a wheel engaged with said pusher member, and a clockspring in said first handle for rotating said wheel to urge said pusher member forward.

17. The instrument in accordance with claim 14 in which said means for moving said row of clips forwardly includes a pusher member in said first handle for pushing against the last clip in the guideway, a wheel engaged with said pusher member, a cord wound around a portion of said wheel, and a compression spring connected at one end to said cord, said spring being mounted in said first handle to pull said cord to unwind said cord from said wheel and thereby rotate said wheel to urge said pusher member forward.

18. The instrument in accordance with claim 14 in which said means for moving said row of clips forwardly includes a flexible tape with embossed, spaced-apart projections along the length of the tape and a wheel adapted to engage said projections.

19. The instrument in accordance with claim 14 in which said escapement means includes a spool mounted for rotation in said first handle jaw and having a forward flange and a rearward flange that are each adapted to engage said engagement means of said clip.

20. A scissors-type medical instrument for repeatedly applying a plurality of ligating clips seriatim about tissue wherein each said clip is initially provided in an open state and wherein each said clip comprises first and second legs which are joined at a leg connection end of the clip and which are spaced apart at their distal ends, each said clip having a base extending along said first leg from the distal end of said leg and terminating short of said clip leg connection end whereby said leg connection end of the clip projects rearwardly of said base to define an open recess adjacent the rearward end of said base below said leg connection end, said clip base including guide means for slidably engaging a portion of said instrument, said instrument comprising:

first and second handles mounted together for pivotal movement about a pivot axis, each said handle extending forwardly beyond the pivot axis to form a clip closing jaw, said jaws having opposing clip engaging faces;

said first handle including a guideway for receiving a plurality of said open clips in a single row with the clips arranged in end-to-end relationship with the distal end of said first leg of one clip abutting the leg connection end of the next forwardly adjacent clip, said first handle including clip retaining means along said guideway for engaging said clip base guide means to retain said clip in sliding engagement within said first handle in said guideway;

means for moving said row of clips forwardly along said guideway to said jaws;

a gate at said first handle jaw mounted for rotation about a longitudinal axis between a first orientation and a second orientation, said gate including a forward flange adjacent the forward end of said first handle jaw, said forward flange projecting in front of said guideway and defining a segment cut away to permit passage of a clip therepast when the gate is in said first orientation but preventing the passage of a clip therepast when said gate is in said second orientation, said gate having a rearward flange spaced rearwardly from said forward flange by a distance substantially equal to the length of the base of a clip, said rearward flange projecting into said guideway and defining a segment cut away to permit the passage of a clip therepast when said gate is in said second orientation but preventing the passage of a clip therepast when said gate is in said first orientation;

a rod extending rearwardly from said gate along said first handle and adapted to rotate about a longitudinal axis coincident with the rotational axis of said gate, said rod having a drive portion projecting laterally at an angle relative to the longitudinal axis of said rod; and an upper engaging member carried by said second handle and a lower engaging member carried by said second handle, said first and second engaging members being spaced apart and receiving between them said drive portion of said rod whereby, (1) when said first and second handles are moved apart, said upper engaging member engages said drive portion of said rod and rotates said rod in a first direction to rotate said gate to said second orientation in which said forward flange blocks further forward feeding of the first clip in the row of clips and thereby maintains said first clip in the region of said jaws and, (2) when said first and second handles are moved toward one another, the front clip in the row of clips within the region of the jaws is squeezed together and closed and said lower engaging member engages said drive portion of said rod and rotates said rod to rotate said gate in a second, opposite direction to said first orientation in which said forward flange permits passage of said closed clip beyond said forward flange as said jaws are subsequently opened by moving said handles apart an amount sufficient to provide clearance around the closed clip but by an amount insufficient to again engage said drive portion of said rod with said upper engaging member.

* * * * *